(12) United States Patent
Murray

(10) Patent No.: US 11,656,449 B2
(45) Date of Patent: May 23, 2023

(54) IMAGING SYSTEM AND METHOD

(71) Applicant: 3D-Oscopy LTD, Milton Keynes Village (GB)

(72) Inventor: Neil John Murray, Milton Keynes (GB)

(73) Assignee: 3D-Oscopy Ltd, Milton Keynes Village (GB)

( * ) Notice: Subject to any disclaimer, the term of this patent is extended or adjusted under 35 U.S.C. 154(b) by 0 days.

(21) Appl. No.: 16/976,668

(22) PCT Filed: Feb. 28, 2019

(86) PCT No.: PCT/GB2019/050571
§ 371 (c)(1),
(2) Date: Aug. 28, 2020

(87) PCT Pub. No.: WO2019/166818
PCT Pub. Date: Sep. 6, 2019

(65) Prior Publication Data
US 2021/0003836 A1  Jan. 7, 2021

(30) Foreign Application Priority Data

Feb. 28, 2018 (GB) .................................. 1803286

(51) Int. Cl.
G02B 23/24 (2006.01)
A61B 1/00 (2006.01)
(52) U.S. Cl.
CPC ....... *G02B 23/243* (2013.01); *G02B 23/2484* (2013.01); *A61B 1/00163* (2013.01)
(58) Field of Classification Search
USPC ......................................................... 348/65
See application file for complete search history.

(56) References Cited

U.S. PATENT DOCUMENTS

| 3,221,593 A | 12/1965 | Ferris |
| 6,063,023 A | 5/2000 | Sakiyama |
| 6,190,308 B1* | 2/2001 | Irion ............... H04N 1/401 600/921 |

(Continued)

FOREIGN PATENT DOCUMENTS

| DE | 102016112010 A1 | 9/2017 |
| EP | 3285232 A1 | 2/2018 |

(Continued)

OTHER PUBLICATIONS

Great Britain Search Report issued in related GB Patent Application No. 1803286.2 dated Nov. 29, 2018, Patents Act 1977: Further Search Report under Section 17(6), 2 pages.

(Continued)

*Primary Examiner* — Behrooz M Senfi
(74) *Attorney, Agent, or Firm* — Brian J. Colandreo; Jeffrey T. Placker; Holland & Knight LLP

(57) ABSTRACT

An imaging device (010, 10, 110) comprises a first optical system (020, 20, 120) at a distal end of the imaging device, a second optical system (080, 80, 180) towards the proximal end of the imaging device, and a sensor (074, 74, 174) at the proximal end of the imaging device. The first and second optical systems and the sensor are aligned along a common longitudinal axis. The first optical system is or comprises one or more reflective and/or refractive optical components (24, 124; 22, 122) symmetrically and/or coaxially arranged with respect to the longitudinal axis, and the second optical system comprises one or more reflective and/or refractive optical components (24, 124; 22, 122) for focussing incident light towards the sensor. A calibration system (200) and method for calibrating such an imaging device, and a method of processing image data obtained from such an imaging device are also provided.

9 Claims, 11 Drawing Sheets

(56) References Cited

U.S. PATENT DOCUMENTS

| | | | |
|---|---|---|---|
| 7,018,331 B2* | 3/2006 | Chang | A61B 1/00059 385/101 |
| 2002/0022767 A1* | 2/2002 | Dohi | G02B 5/06 600/137 |
| 2003/0004398 A1* | 1/2003 | Takahashi | A61B 1/00059 600/109 |
| 2006/0018012 A1 | 1/2006 | Smith et al. | |
| 2007/0161853 A1* | 7/2007 | Yagi | A61B 1/00009 600/117 |
| 2008/0247039 A1 | 10/2008 | Mizusawa | |
| 2009/0010507 A1 | 1/2009 | Geng | |
| 2015/4022988 | 8/2015 | Kisner et al. | |
| 2015/0346115 A1 | 12/2015 | Seibel et al. | |
| 2016/0088204 A1 | 3/2016 | Liang et al. | |

FOREIGN PATENT DOCUMENTS

| | | |
|---|---|---|
| GB | 2030313 A | 4/1980 |
| GB | 2099603 A | 12/1982 |
| GB | 2333595 A | 2/1998 |
| WO | 2008115684 A1 | 9/2008 |
| WO | 2011143264 A1 | 11/2011 |
| WO | 2019166818 A1 | 9/2019 |

OTHER PUBLICATIONS

Great Britain Search Report issued in related GB Patent Application No. 1803286.2 dated Nov. 29, 2018, Patents Act 1977: Further Search Report under Section 17(6), 3 pages.

Great Britain Search Report issued in related GB Patent Application No. 1803286.2 dated Aug. 30, 2018, Patents Act 1977: Combined Search and Examination Report under Section 17 and 18(3), 9 pages.

International Search Report and Written Opinion issued in PCT Application Serial No. PCT/GB2019/050571 dated Jul. 22, 2019, 14 pages.

\* cited by examiner

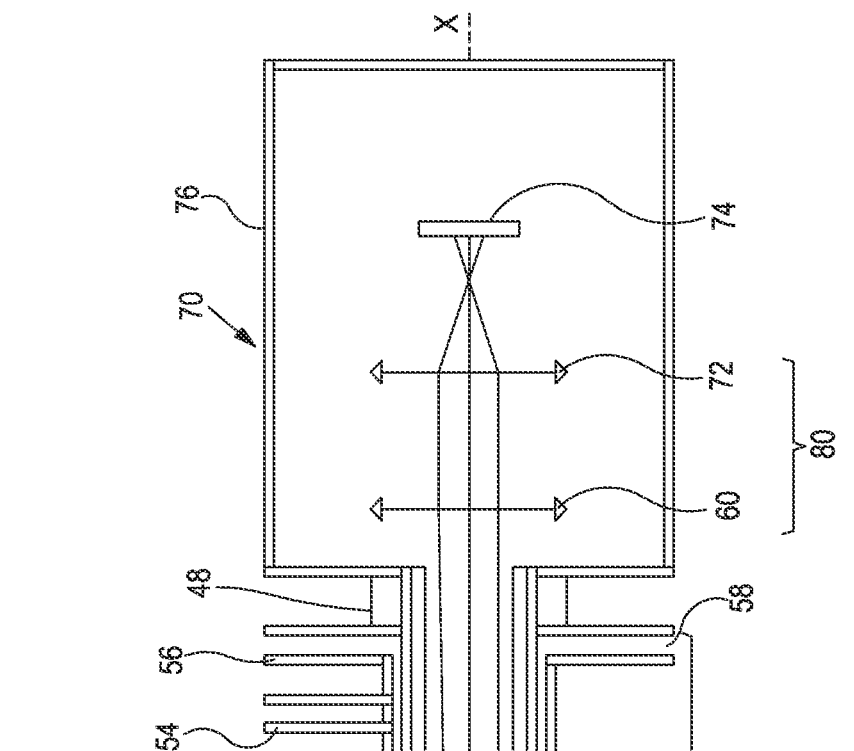
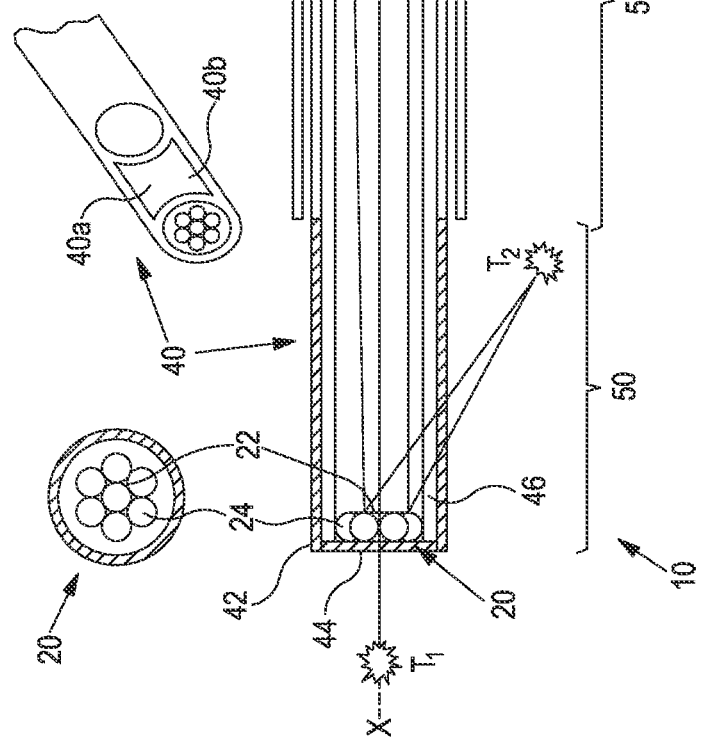
FIG. 2B  FIG. 2C
FIG. 2A

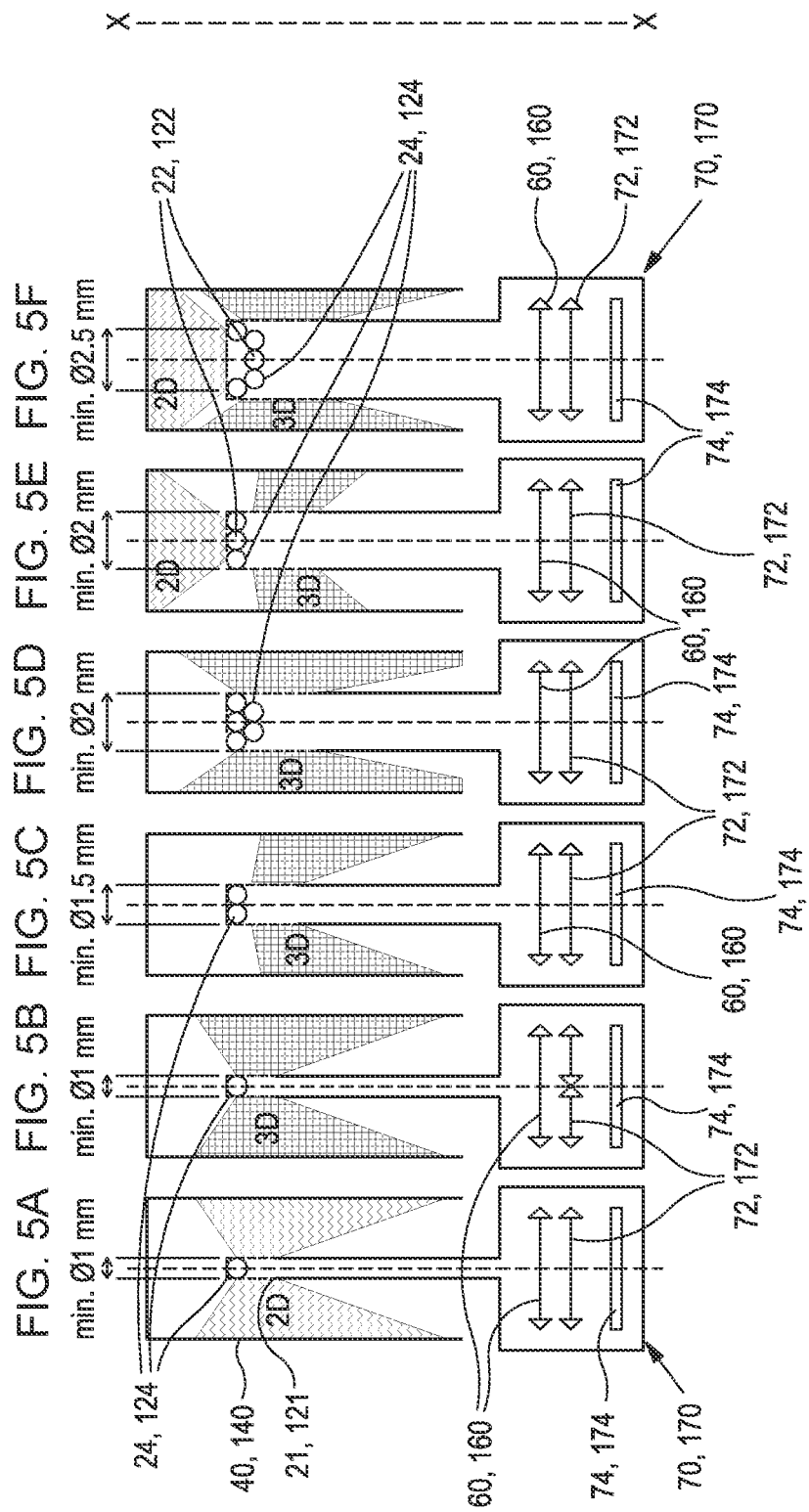

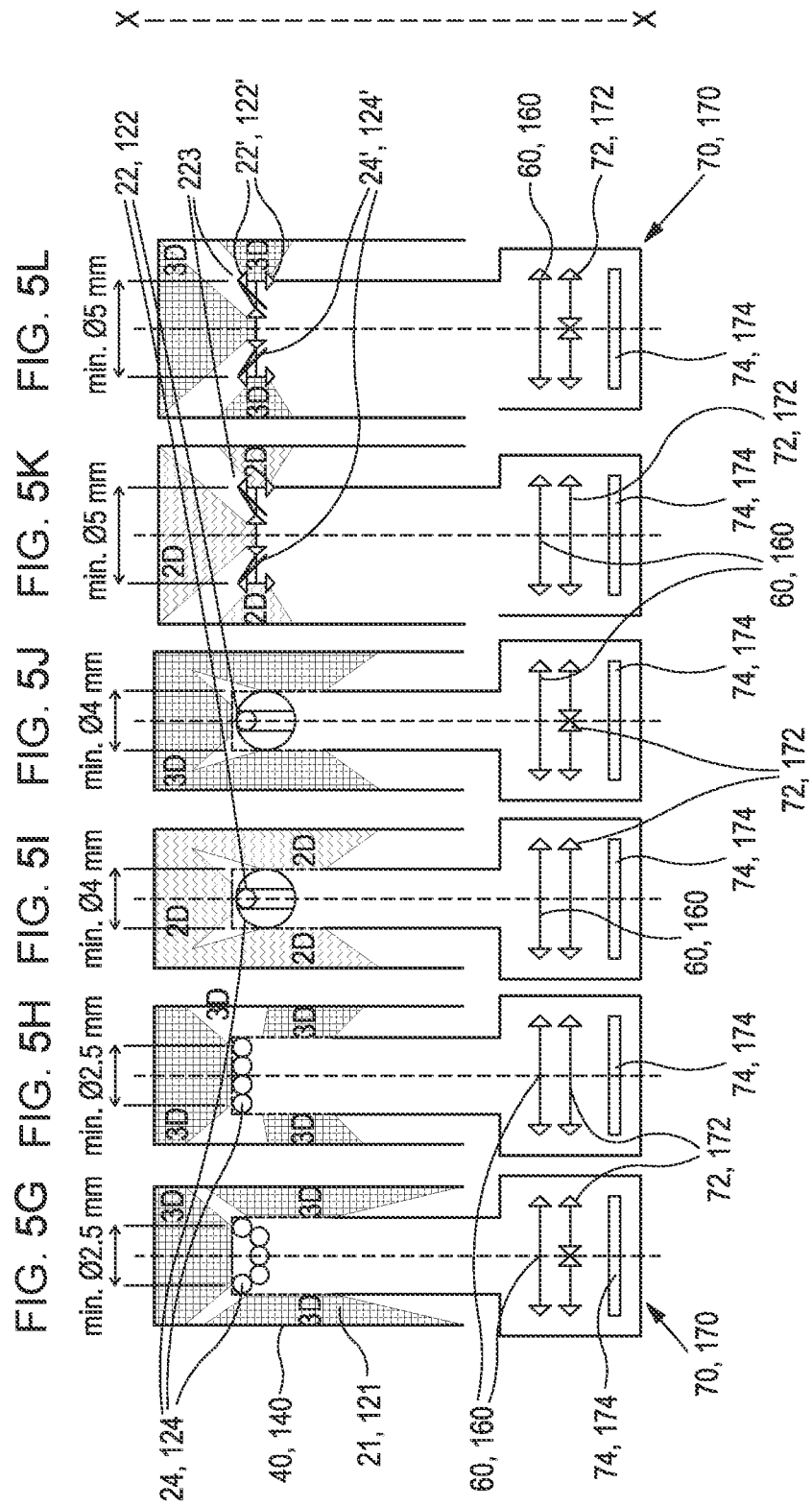

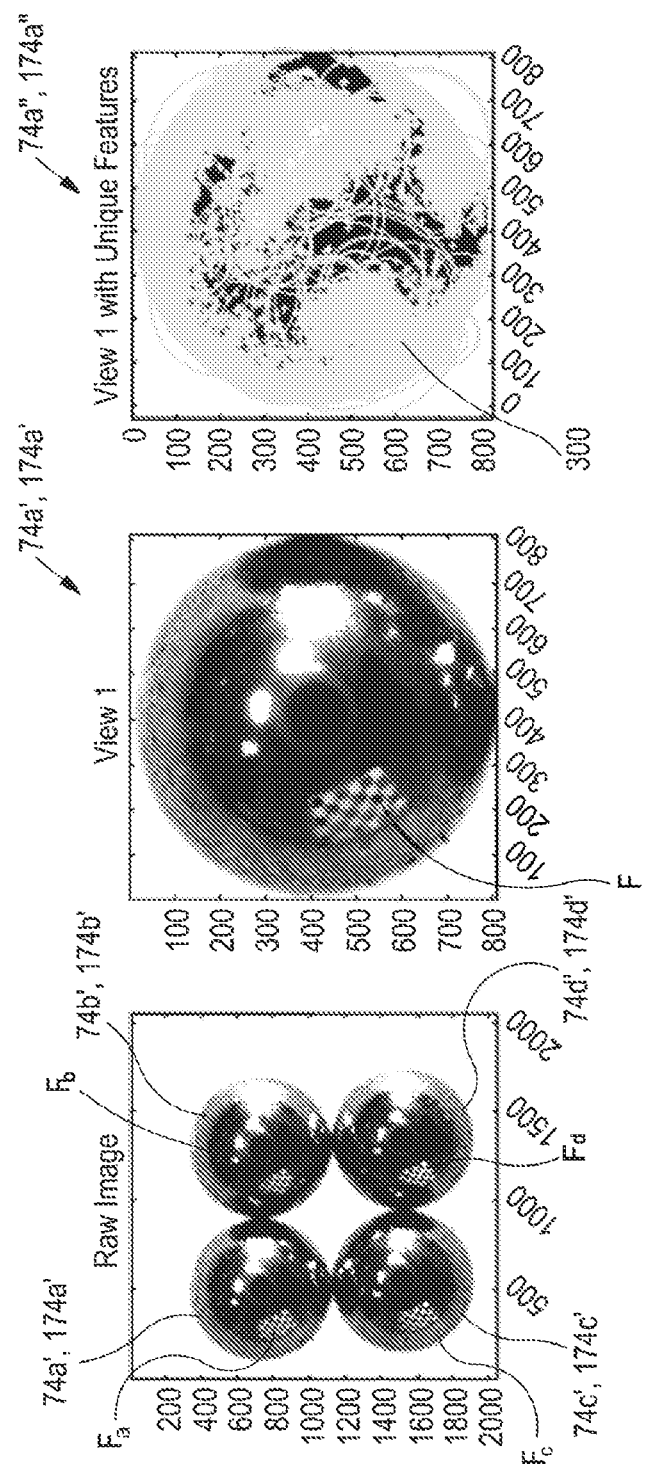

2433 Features Matched Between View 1 and View 4

2433 Features Matched Between View 3 and View 4

2433 Features Matched Between View 1 and View 3

2433 Features Matched Between View 2 and View 4

2433 Features Matched Between View 1 and View 2

2433 Features Matched Between View 2 and View 3

IMAGING SYSTEM AND METHOD

CROSS-REFERENCE TO RELATED APPLICATIONS

The subject application is a U.S. National Stage application of International Application No. PCT/GB2019/050571, filed on 28 Feb. 2019, which claims the priority of Great Britain Patent Application No. 1803286.2, filed on 28 Feb. 2018. The contents of all applications are herein incorporated by reference in their entirety.

TECHNICAL FIELD

The present invention relates to an imaging system and method and, in particular but not exclusively, to an imaging system and method for generating a 3D representation of an imaged scene. Systems and methods of calibrating and/or processing measured data are also provided.

BACKGROUND TO THE INVENTION

Imaging techniques such as endoscopy and borescopy are widely used to obtain information on internal structures e.g. inside a person's body, as a borescope, for architectural or archaeological excavations, safe bomb disposal etc. Typically an endoscope or borescope has a light delivery system to illuminate a target and a lens system for transmitting light from the target to a sensor or camera.

Most endoscopes and borescopes permit light to enter through a transparent window at the front or offset by some angle to the side. Whilst readily available and relatively inexpensive, simple endoscopes or borescopes of this kind run the risk of not seeing a potentially relevant target due to the narrow field of view. Developments have been made to include a reflective optic such as in US 20160088204. This allows a wider range of viewing angles, but some angles may be obscured by the structure of the device.

However, endoscopes, borescopes and other similar imaging devices are still restricted by the angular view and the data that is obtainable using them.

Some endoscopes can be rotated to change the target being viewed, but this requires manipulation of the endoscope about its longitudinal axis. This may be uncomfortable for the patient or operator and the endoscopy process may take longer which is undesirable because it prolongs or increases the discomfort and cost of endoscopy.

Some endoscopes allow the target view to be altered by manipulating the direction of the imaging window with respect to the longitudinal axis of the endoscope. However, this requires additional mechanisms to change the direction and prolongs the procedure and/or increases the discomfort.

Some existing endoscopes are provided with a separate, additional imaging system to obtain one or more radial or sideways views in addition to the forward view. However, this results in a more bulky endoscope and with views limited by structural parts. Endoscopes contain complex and precision optical components and efforts to date to try to increase their capabilities have led to devices that have become more complex and expensive and which are still restricted by the angular view and the data that is obtainable using them.

Aspects and embodiments of the present invention have been devised with the foregoing in mind.

SUMMARY OF THE INVENTION

According to a first aspect of the present invention there is provided an imaging device comprising a first optical system at a first (e.g. distal or front) end of the imaging device. The imaging device further comprises a second optical system at a second or proximal end e.g. behind the first optical system in the imaging device. The imaging system may further comprise a sensor at the proximal end (e.g. at a rear end) of the imaging device. As such, there is preferably provided a first optical system at a first (front or distal) end, a sensor at the opposite (proximal) end, and a second optical system in between the first optical system and the sensor. The first optical system, the second optical system and the sensor are preferably aligned along a common longitudinal axis. The first optical system may comprise a reflective optical component and a refractive optical component symmetrically/coaxially arranged, or offset, with respect to the longitudinal axis. The first optical system may comprise one or more reflective optical components. The second optical system may comprise one or more refractive optical components for focussing incident light towards the sensor. The first optical system may comprise one or a plurality of reflective and/or refractive optical components. The second optical system may comprise one or a plurality of reflective and/or refractive optical components. The first optical system may comprise a plurality of reflective optical components and/or the second optical system may comprise a plurality of reflective optical components. The first and/or second optical system may each comprise a combination of at least one reflective and at least one refractive optical component. In embodiments, 3D imaging e.g. "stereovision" may be achieved by having a plurality of reflective or refractive elements in either or both of the first and second imaging systems.

Where there is a plurality of reflective and/or refractive optical components, each plurality may be or comprise a number of optical components arranged in the same plane, or not in the same plane.

The first and/or second optical system may be configured to image an object in the axial and/or radial direction. The sensor may be configured to sense light that has passed through the first and/or second optical systems.

Aspects and embodiments of the invention advantageously provide the ability for simultaneous imaging to the front (or forward) (axial) and side (radial) (and optionally extending axially in a substantially rearward and/or substantially forward direction) without the need to rotate or mechanically articulate (e.g. bend). This enables any and all features to be imaged and measured. The invention therefore, advantageously, provides for imaging in three dimensions without the need to move or manipulate the device or provide additional imaging devices.

An overall aim of the invention is to achieve an imaging device such as an endoscope or borescope that has wide field (volume) of view in the axial and radial (forward and side, and optionally extending to rearward) directions, with limited obstruction to field of view and with, in some cases, the ability to determine a location in 3-dimensional space of any subject feature within one or more or all of these fields of view.

Aspects and embodiments of the invention provide imaging in three dimensions, in comparison to simple, known endoscopes where images am produced in two dimensions and give limited perception of depth and are unable to measure the size of features.

Aspects and embodiments of the present invention can advantageously image in three dimensions. Some known endoscopes can image in three dimensions through the use of stereo optical systems. This increases the size of the system, which limits their use and/or may increase the discomfort in use. And still such endoscopes are limited by their field of view and the need to ensure that the optical system is directed at the target of interest.

In some embodiments, 3-D imaging (with increased depth perception and ability to measure feature sizes) is provided in the side (radial) view.

In some embodiments, 3-D imaging (with increased depth perception and ability measure feature sizes) is instead/additionally provided in the forward (axial) view.

The 3-D imaging the invention provides for can advantageously be achieved in a single image or single exposure or readout. This can be achieved by capturing multiple views of the same or substantially the same object or scene and optionally from a plurality of different directions e.g. a plurality of forward, and/or a plurality of side and/or a plurality of backward views, with each view obtained from a different perspective (due to the provision of a plurality of reflective and/or refractive optical components). Any disparity and/or distortion in these images can then be exploited to generate valuable 3-dimensional information about an object or the imaged scene. The optics provide multiple forward views and/or multiple side (and/or backward) views. The multiple views in the forward, side or back view are from (slightly) different perspectives from each other and so any disparity between them can be exploited to generate a 3D representation of an imaged feature/object/scene.

Multiple views of an object/scene can be obtained by providing a plurality of reflective or refractive elements or (radial) planes of reflective or refractive elements, each of which is configured to be able to reflect or refract an image of an object or scene. Due to the different physical locations of each element/plane, the image of each that is received by the sensor will depict the object/scene from a slightly different viewpoint. A feature on the object/In the scene will be viewed differently at the sensor e.g. it will be viewed/captured at a slightly different position and/or the shape, configuration and or size of the object/scene will be imaged differently at the sensor. A "disparity" between the position of the feature/scene as it reflects/refracts off of each element or plane may occur in one view compared to another view. The feature/scene as imaged at the sensor will be "distorted" due to the different angles at which each is imaged i.e. by how the image of the feature/scene is distorted by the optical element.

The disparity/distortion (which may be referred to from hereon simply as "disparity" for simplicity) may be generated by a plurality of reflective elements optionally arranged as one or more planes of one or more reflective elements (e.g. ball bearings) at or in the first optical system at the distal end (i.e. at the opposite end to the image sensor/camera).

The disparity/distortion may additionally or alternatively be generated by a plurality of refractive elements optionally arranged as one or more planes of refractive elements at or in the first optical system at the distal end. A combination of reflective and refractive elements may be provided in one or more planes at or in the first optical system at the distal end.

In an embodiment, instead of a plurality of discrete reflective and/or refractive elements, a homogeneous or unitary optical element may be provided which incorporates the first optical system at the distal end and/or the second optical system at the proximal end. The elements may be profiled to provide a combination of refraction and total internal reflection to provide axial and radial imaging.

The disparity/distortion may also be generated by two or more refractive or reflective elements that may be provided in the same radial plane, the elements being offset from the axial direction, and placed at or in the second optical system at the proximal end (end near to image sensor/camera). Alternatively, the elements may be provided not in the same radial plane.

Embodiments of the imaging system advantageously provide a monolithic or a single structure that is capable of 3D imaging, unlike known devices that require additional optical components/systems or the need for additional optical components and/or more complicated mechanical manipulation to image in 3D.

The first optical system may be or comprise a central refractive element e.g. a lens such as a convex lens. The first optical system may also or instead comprise one or more reflective elements.

The one or more reflective elements may surround the lens in one or more planes that are perpendicular to the longitudinal axis (the axial direction) of the imaging device. In an embodiment, the one or more reflective elements is one or more mirrored elements or one or more elements each having a mirrored surface. Each reflective element may be a substantially spherical reflective element such as a reflective ball bearing e.g. made of or coated in metal. Instead one or more reflective elements having a complex shape and/or a profiled reflective surface could be provided.

The one or more refractive elements may be one or more lenses, for example refractive sapphire sphere lenses or a biconvex lens e.g. of glass. In another embodiment, a single reflective element e.g. a (metal) ball bearing is used. The refractive lens, e.g. a sapphire spherical lens, can be placed in or otherwise occupy a bore or hole in the ball bearing. The lens is aligned along the longitudinal (optical) axis. In still another embodiment, the first optical system comprises a monolithic transparent medium configured to permit both refraction of light and total internal reflection. The monolithic medium may be configured to comprise or create a forward-facing lens element and combination of total internal reflection and refractive surfaces to allow sideward viewpoints substantially 360 degrees about the longitudinal axis.

The second optical system may be or comprise a refractive e.g. convex lens or lens group. Alternatively the second optical system may be or comprise one or more optic fibres. Alternatively the second optical system may be or comprise one or more reflective optical components.

One or more additional optical systems that are or comprise a refractive e.g. convex or concave lens may also be provided. Alternatively each one or more optical system may be or comprise one or more optic fibres.

The imaging device may further comprise a sensor or camera, for sensing light that has passed through the imaging device. The reflective and/or refractive optics are configured and/or located so as to focus light entering the imaging device from an external location onto the sensor/camera.

The imaging device may have a forward window, e.g. formed of a transparent material, to permit light to enter into the imaging device through the lens/lenses of the first optical system along the longitudinal axis or at an angular range about the longitudinal axis. The imaging device may further be configured to permit light to enter from other angles. The imaging device may be provided with an open, semi-open or transparent housing that permits light to enter the imaging device from a greater range of angles than just through the forward window. The semi-open structure may be provided as a transparent tube, enclosure or sheath, e.g. formed of glass. The transparent enclosure may be surrounded by a rigid cage or surround that is substantially open. The cage may be formed of a minimal amount of rigid material e.g. steel to provide mechanical strength. The sheath may advantageously be waterproof and/or sealed. Preferably at least the front portion of the imaging device is configured in this way. Light entering the system from an angle that is not substantially along the longitudinal axis will be reflected by the reflective elements and may in full or in part be reflected towards the second optical system. Where the first optical system comprises one or more ball bearings (or suchlike), the field of view extends all the way to the rear of the system (although the outside view may be occluded by other components of the system). In practice this could be up to about 80 degrees from the plane about the longitudinal axis where the first optics sit. In other embodiments, e.g. those using monolithic optics, it may be about 30 degrees from the first optical plane (the total internal reflection off the monolithic material requires this to stay above the critical angle).

The rest of the imaging system housing may be non-open or non-transparent e.g. formed of stainless steel.

The imaging device may be provided with one or more sources of illumination, for directing light in the forward and/or angular directions to illuminate the area to be imaged.

The imaging device may be provided with a fluid inlet and a fluid outlet. Cleaning fluid e.g. water, air, saline etc. may be provided to the inlet, directed around the imaging device to clean and/or lubricate the relevant parts such as the forward window and/or the open front portion to ensure accurate imaging.

The sensor may be a camera such as a CMOS or CCD camera comprising an array of sensing elements or pixels.

The arrangement of aspects and embodiments advantageously provides a combination of refractive and reflective optics to capture multiple images of a target, feature or scene. The refractive optics may comprise one or more lenses or dioptrics. The reflective optics may comprise one or more mirrors or catoptrics. The optics capture multiple images of a target, feature or scene. Processing the images obtained can advantageously generate rich and valuable data products including 3D representations of the target, feature or scene.

Aspects and embodiments of the invention may utilise both (catadioptric) optical hardware and software to post-process the images. Aspects and embodiments provide for calibrating the optical system. This advantageously simplifies the software needed, and means it is more efficient—it is faster and/or requires less processing power.

Advantageously, the technology can be implemented in a compact form, making it suitable for imaging inside restricted spaces—for instance, in endoscopy applications. Of particular interest is medical endoscopy, which can be performed using rigid, flexible and capsule endoscopes. The technology can be applied to endoscopes of rigid, flexible and capsule types. The use of optic fibres for/In one or more of the optical systems may facilitate this.

The technology offers various advantages over existing devices. For example, the reflective optic ("sideways" or 'backwards looking') enables imaging in places inaccessible to conventional refractive ('forwards looking') optic. Additionally or alternatively, aspects and embodiments of the invention provide a very wide panoramic field of view for imaging, which reduces the time required for imaging (which is both of patient and practitioner benefit) and the skill level required (again both of patient and practitioner benefit).

According to a second aspect of the invention, there is provided a calibration system for an imaging device such as, but not limited to, the imaging device of the first aspect. The calibration system may be configured to move (e.g. rotate) with respect to the imaging device. The calibration system may comprise a rotatable stage or support. It may also comprise one or more test patterns or light sources mounted perpendicularly to the stage so as to be rotatable with the stage. Alternatively, the arrays could remain fixed in position (i.e. no need for the stage to be rotatable) and the imaging device could be mounted on a rotatable stage or support. The calibration system may further comprise a control unit for selectively activating and/or deactivating the one or more light sources at a plurality of angular positions and distances from the longitudinal axis as the stage is rotated.

According to a third aspect of the present invention there is provided a method of calibrating an imaging device. The method may be used to calibrate the imaging device of the first aspect. The imaging device of the first aspect may be configured to be used with the system of the second aspect and/or the method of the third aspect. The method comprises positioning an imaging device near a calbration device having one or more light sources mounted such that their longitudinal axes extend in the same direction as the longitudinal axis of the imaging device. The method further comprises selectively activating and/or deactivating the one or more light sources at a plurality of angular positions as the calbration device is rotated relative to the imaging device (or vice versa). The method further comprises using a sensor or camera in the imaging device, sensing light emitted from the light source.

The light source or sources may be or comprise an array of individually controllable light sources e.g. an OLED or LED/pixel array.

The arrays may be mounted to a rotatable stage or support, or the imaging device may be mounted to a rotatable stage or support. Alternatively the light sources could be freestanding or fixed to multiple translation stages.

Preferably a plurality of light source arrays are utilised, positioned at different distances from the centre of the stage. In an embodiment, the stage is substantially circular and the LED arrays are positioned at different radii from the centre of the stage (If used) and/or the central axis of the imaging device.

In use, an imaging device is positioned with respect to the sensor arrays of the calibration system, preferably aligned in the perpendicular direction with the centre of the stage. A single light element (e.g. a single LED/pixel) is then turned on and the image of that light is recorded by the sensor/camera of the imaging device. The imaging device or light arrays (e.g. mounted on a stage) are rotated by a predefined increment and another reading is taken. Further equal increments in angular rotation are performed and the image recorded by the sensor for each increment. The process is repeated for some or all of the other light elements of the calibration array. The data collected by the sensor provides imaged references to known measurements in 3D space about the device. This is because each LED/pixel is located at a particular position in 3D space and rotating the stage for measuring the same LED light gives rotational information in a single plane. Illuminating other LEDs in the same or different arrays, and at different angular and perpendicular (vertical) positions gives numerous 3D positional measurements. For each pixel/LED illuminated in this way, the image taken (or data indicative of the sensor/camera element(s) activated during measurement) can be recorded and cross-referenced to the LED position in 3D space. It will therefore be appreciated that, within the measurement/calibration constraints imposed by the size of the LED arrays, 3D reference position/Imaging data e.g. a reference or lookup table can be produced.

According to a fourth aspect of the present invention, there is provided a method of processing image data obtained from an imaging device. The method comprises providing a plurality of images, e.g. 2D images, obtained from an imaging device. The method further comprises interrogating a first image of the plurality of images for unique features. The method may further comprise matching common features identified in multiple images. The identified common features may be referenced with stored data (e.g. calibrated 3D positional data) to determine a 3D location from the identified common features.

The method of the fourth aspect may be used with the imaging device of the first aspect. The imaging device of the first aspect may be configured to be used in the method of the fourth aspect.

The method may further comprise obtaining the plurality of 2D images from an imaging device. The imaging device may be the imaging device of the first aspect. The method may comprise illuminating the light source. The method may comprise rendering the images.

The method may comprise searching for the same unique features in one or more of the other 2D images.

The method may comprise matching common features identified in such multiple images. The identified common features may be referenced with stored data (e.g. calibrated 3D positional data) to determine a 3D location from the identified common features.

The matching and/or referencing may comprise looking for and optionally identifying one or more disparities between two or more of the captured images.

The identifying one or more of said disparities may comprise identifying or calculating differences in the location, size, shape and/or other parameters associated with the unique feature(s).

The first, second, third and/or fourth aspect, and/or any one or more embodiments thereof, may be provided separately, or in any combination.

"Three-dimensional" as used herein is intended to refer to a determined target/origin location in space and to imaging in both the forward and sideways and/or backward directions.

"Computer program" as referred to here and elsewhere in the specification refers to a program operable to run on a computer or other processing device e.g. a mobile phone (including an iPhone), a tablet (including an iPad), or be integrated on or in the imaging device itself etc.

The computing or processing device may be configured to host instructions for enabling processing of the output signal from the device. The system may have an input/output data interface. The system may include a processor, a storage device, and a non-transient machine-readable storage medium. The machine-readable storage medium may include instructions which control how the processor receives input data and transforms the input data (the electrical signal) into output data e.g. on the screen, a connected printing device or via an audio output. The machine-readable storage medium in an alternate example embodiment is a non-transient computer-readable storage medium.

In an embodiment, a computer program is provided which, when run on the computing or processing device, causes the computer to perform any method disclosed herein. The computer program may be a software implementation, and the computer or device it runs on may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples. The software implementation may be an assembly program.

The computer program may be provided on a computer readable medium, which may be a physical computer readable medium, such as a disc or a memory device, or may be embodied as a transient signal. Such a transient signal may be a network download, including an internet download.

Features which are described in the context of separate aspects and embodiments of the invention may be used together and/or be interchangeable. Similarly, where features are, for brevity, described in the context of a single embodiment, these may also be provided separately or in any suitable sub-combination. Features describes in connection with the device may have corresponding features definable with respect to the method(s) and the computer program and these embodiments are specifically envisaged.

Embodiments of the invention will now be described with reference to the Figures of the accompanying drawings in which:

FIG. 1 schematically illustrates an imaging device or system according to the invention;

FIGS. 2A, 2B and 2C show an imaging device or system according to a first embodiment;

FIGS. 5A to 5L show further embodiments of an imaging device or system;

FIGS. 10A, 10B and 10C show images taken during use; and

DETAILED DESCRIPTION OF EMBODIMENTS OF THE INVENTION

Figure 1:
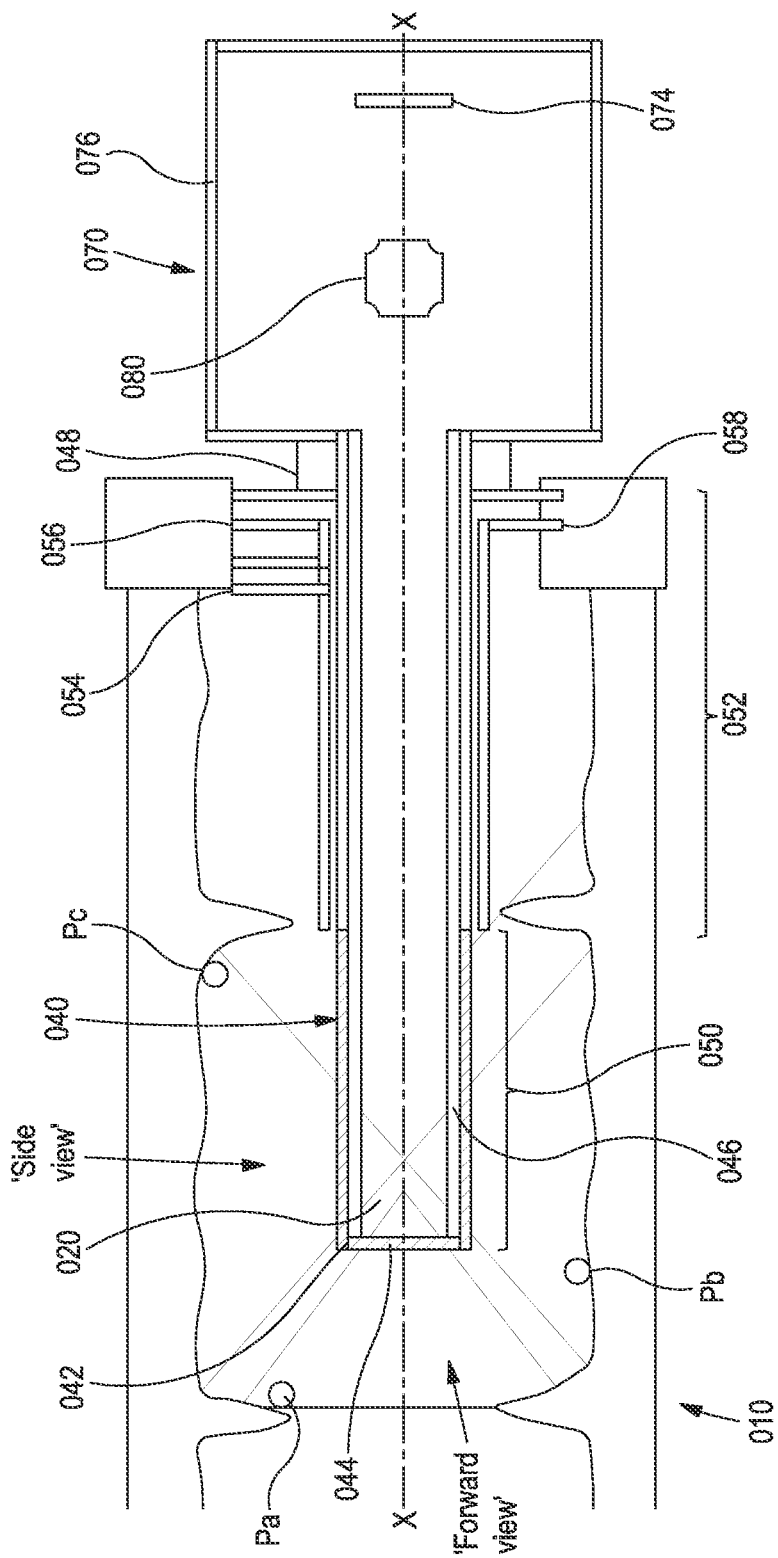

FIG. 1 shows an imaging system 010. The imaging system 010 comprises a first (distal) optic or set of optics 020. The first set of optics 020 may comprise one or more refractive and/or reflective optical elements. The optics 020 may be supported by a support structure (not shown in FIG. 1; equivalent support structure 21 is shown in FIGS. 5A-5L). The support structure 21 may be transparent at least in part and/or opaque at least in part.

The optic(s) 020 is (are) housed within a longitudinal enclosure 040 and are aligned along the central longitudinal axis X-X of the enclosure 040. The (radial) plane of the first optic 020 is transverse to the longitudinal axis X-X (the axial direction). The first optic 020 is positioned at or near a first end 042 of the enclosure 040. The first end 042 of the enclosure has a window or opening 044 also aligned transverse to the longitudinal axis X-X. The window 44 could be plain glass or plastic (or other suitable transparent or semi-transparent material), or a focusing lens. As such, the planes of the first optic 020 and the window 044 are parallel to each other. The window 044 is transparent so as to allow light to enter the system 010. The window 044 may be or comprise glass or a plastics material.

The enclosure 040 is tubular, closed at the first end 042 save for the window 044 at the first end 042. The enclosure comprises a sleeve 046 of transparent material e.g. glass or plastic extending from the first end 042 to a second end 048. The sleeve 046 is sealed and may be formed of clear glass or plastic, to prevent contamination of the optical surfaces. A first portion 050 of the enclosure 040 starting at the first end 042 and extending towards a second end 048 of the enclosure 040 surrounds the sleeve 046 and is semi-open e.g. contains one or more cutouts or is of a frame or cage-like structure and may e.g. be formed of stainless steel. A second portion 052 of the enclosure starting from the innermost end of the first portion 050 and extending to the second end 048 is formed of a solid or non-transparent material e.g. solid stainless steel.

A light source (not shown) and a light tube 054 may be provided to direct light towards a subject to illuminate it for imaging. The light source could be external to the endoscope and light transmitted inside via an optical light path, or the light source could be inside the imaging device. The light source may be an LED e.g. a white LED. A colour filter array (e.g. a Bayer filter mosaic) may be used to produce a colour image. The light source may be a repeating and/or alternating sequence of monochromatic wavelengths. For example, red, green and blue light can be used. The resultant images can be combined to achieve a colour image. Additional wavelengths can be input to achieve other outputs. For example, where the system 010 is an endoscope, additional wavelengths can be input for advanced diagnosis techniques e.g. phosphorescent biological markers, oxy/deoxyhemoglobin, short wave infrared for sub-surface imaging etc.

The enclosure 040 also has a fluid inlet 056 for directing e.g. pumping a fluid such as air, water and/or saline along the enclosure 040 to help keep it clean. The enclosure 040 may also have a fluid outlet 058 for removing used fluid from the system 010.

At the second end 048 of the enclosure 040, there is a light capture system 070. The light capture system 070 comprises a second (proximal) optical system 080. The light capture system 070 comprises the second optical system 080 and a light sensor such as a CMOS camera sensor 074. The second optical system 080 and the sensor 074 are housed in a housing 076.

The imaging device 010 can image features of interest such as polyps Pa, Pb, Pc in a body structure with both "forward" and "side" views. The "forward" view is or includes a volume or cone around the optical axis X-X in the forward axial direction. The "sideways" view is or includes a range of angles in zenith either side of the axial plane. The sideways view may also extend toward the backward direction (although it will be appreciated that a full 360° volume cannot be achieved due to the arrangement of the instrumentation itself. A full 360 degrees in side view around the longitudinal axis is possible, but a full 360 degrees in zenth is not possible because of obstruction due to the presence and location of the optical components in the device/system.

In use, a target or feature such as a polyp Pa can be imaged through the forward view. In use, a target such as a polyp Pb and polyp Pc can be imaged through the side (and or backward) view.

Light reflected from the target Pa/Pb/Pc enters the enclosure 040 through window 044. The reflected light is transmitted through the first optical system 020 to the second optical system 080 and is captured by the sensor 074. An image (not shown) and/or image data from the sensor 074 can be transmitted to a computing/processing device for further processing in a conventional manner.

FIGS. 2, 3, 4 and 5 show more detailed, specific embodiments of the general depicted in FIG. 1.

FIG. 2A shows an imaging system 10. The imaging system 10 comprises a first optic or set of optics 20. The first set of optics 20 comprises a central refractive optic 22 and a plurality of reflective optics 24. In the embodiment shown, the refractive optic 22 is a lens. The lens 22 is surrounded by a number of reflective elements e.g. spherical reflective elements such as ball bearings 24—six in the embodiment shown. Other reflective elements could be used instead. The reflective elements 24 are arranged around the central lens 22 in a plane, as shown in FIG. 2B. The optics 20 may be supported by a support structure (not shown in FIG. 2; equivalent support structure 21 is shown in FIGS. 5A-5L). The support structure 21 may be transparent at least in part and/or opaque at least in part.

The optic(s) 20 is (are) housed within a longitudinal enclosure 40 and are aligned along the central longitudinal axis X-X of the enclosure 40. The plane of the first optic 20 is transverse to the longitudinal axis X-X. The first optic 20 is positioned at or near a first end 42 of the enclosure 40. The first end 42 of the enclosure has a window or opening 44 also aligned transverse to the longitudinal axis X-X. The window 44 could be plain glass or plastic (or other suitable transparent or semi-transparent material), or a focusing lens. As such, the planes of the first optic 20 and the window 44 are parallel to each other. The window 44 is transparent so as to allow light to enter the system 10. The window 44 may be or comprise glass or a plastics material.

The enclosure 40 is tubular, closed at the first end 42 save for the window 44 at the first end 42. The enclosure comprises a sleeve 46 of transparent material e.g. glass or plastic extending from the first end 42 to a second end 48. The sleeve is sealed and may be formed of clear glass or plastic, to prevent contamination of the optical surfaces. A first portion 50 of the enclosure 40 starting at the first end 42 and extending towards a second end 48 of the enclosure 40 surrounds the sleeve 46 and is semi-open e.g. contains one or more cutouts or is of a frame or cage-like structure and may e.g. be formed of stainless steel. FIG. 2C shows an exemplary semi-open structure. Here, an inner glass tube 40a is surrounded by a steel "cage" or surround 40b that is transparent to the imaging device. In an embodiment, a transparent sheath may be covered or housed within a substantially open cage. The cage advantageously provides mechanical strength. The sheath may advantageously be waterproof and/or sealed. A second portion 52 of the enclosure starting from the innermost end of the first portion 50 and extending to the second end 48 is formed of a solid or non-transparent material e.g. solid stainless steel.

A light source (not shown) and light tube 54 may be provided to direct light towards a subject to illuminate it for imaging. The light source could be external to the endoscope and light transmitted inside via an optical light path, or the light source could be inside the imaging device. The light source may be an LED e.g. a white LED. A colour filter array (e.g. a Bayer filter mosaic) may be used to produce a colour image. The light source may be a repeating and/or alternating sequence of monochromatic wavelengths. For example, red, green and blue light can be used. The resultant images can be combined to achieve a colour image. Additional wavelengths can be input to achieve other outputs. For example, where the system 10 is an endoscope, additional wavelengths can be input for advanced diagnosis techniques e.g. phosphorescent biological markers, oxy/deoxyhemoglobin, short wave infrared for sub-surface imaging etc.

The enclosure 40 also has a fluid inlet 56 for directing e.g. pumping a fluid such as air, water and/or saline along the enclosure 40 to help keep it clean. The enclosure 40 may also have a fluid outlet 58 for removing used fluid from the system 10.

At the second end 48 of the enclosure 40, there is a light capture system 70. The light capture system 70 comprises a second optical system 80. The second optical system 80 comprises a second 60 and third refractive optic 72. The light capture system 70 comprises the second 60 and third refractive optic 72 and a light sensor such as a CMOS camera sensor 74. The second and third optics 60, 72 may each be or comprise a refractive lens. The second optic 60 and third optic 72 and the sensor 74 are housed in a housing 76.

Figure 9:
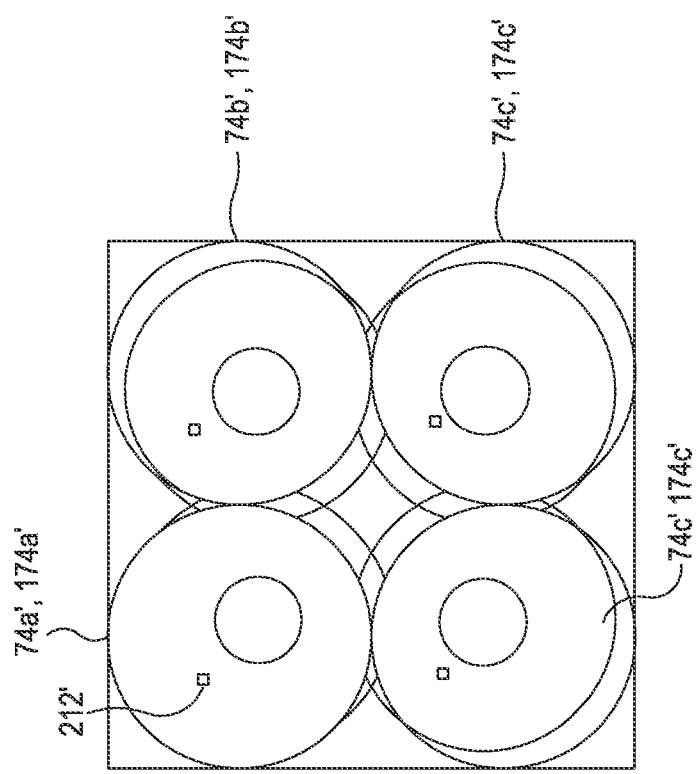
FIG. 9 depicts projection of light onto a sensor of an exemplary system during a calbration operation.

In use, a target $T_1$ can be imaged. Light from the light source is directed via light input 54 towards the target $T_1$. Light reflected from the target $T_1$ enters the enclosure 40 through window 44. The reflected light is transmitted through the first refractive optic 22 to the second refractive optic 60 and further refracted through the lens 72 and is captured by the sensor 74. An image 74' (not shown in FIG. 2 but see e.g. FIG. 9 or 10) and/or image data from the sensor 74 can be transmitted to a computing/processing device for further processing in a conventional manner. The image 74' is transmitted from the sensor 74 to a computer, storage device or similar in any suitable/conventional way. In this example, only a single image of $T_1$ is obtained. If a plurality of suitable lenses is provided at the second optic 60/72, then multiple images of T1 are obtained at sensor 74. This enables a disparity between the images obtained by each lens in the second optical system 80 to be exploited to obtain 3-D information about T1. The plurality of lenses in the second optical system may be a plurality of lenses 72 arranged in the radial plane and with each offset from the axis X-X of FIG. 2.

In the embodiment shown, the target $T_1$ is aligned with and in front of the window 44. However, the semi-open first housing portion 50 and the configuration of the first optic 20 also enables non-aligned targets to be imaged. In the embodiment of FIG. 2, target $T_2$, which is to one side of the enclosure 40, may also be imaged. Light reflected from the target $T_2$ can reach the first optic 20 because the first portion of the housing 50 is semi-open (e.g. as shown in FIG. 2C). The light is then further reflected by the reflective surfaces (ball bearings) 24 towards the sensor 74. As for light reflected from $T_1$, the second optic 60 and third optic 72 disperses the light to the sensor 74. $T_2$ can be imaged in 3D as multiple images are generated by multiple reflective elements in the first optical system 20, which gives disparity/distortion in images recorded at the sensor 74. See also the embodiment in FIG. 5E.

One or more additional refractive optics (not shown) could be included in the planar array to maximize the viewing area and/or provide for 3D imaging/viewing, although a balance may need to be struck to keep the system 10 small.

Figures 3A, 3B, 3C:
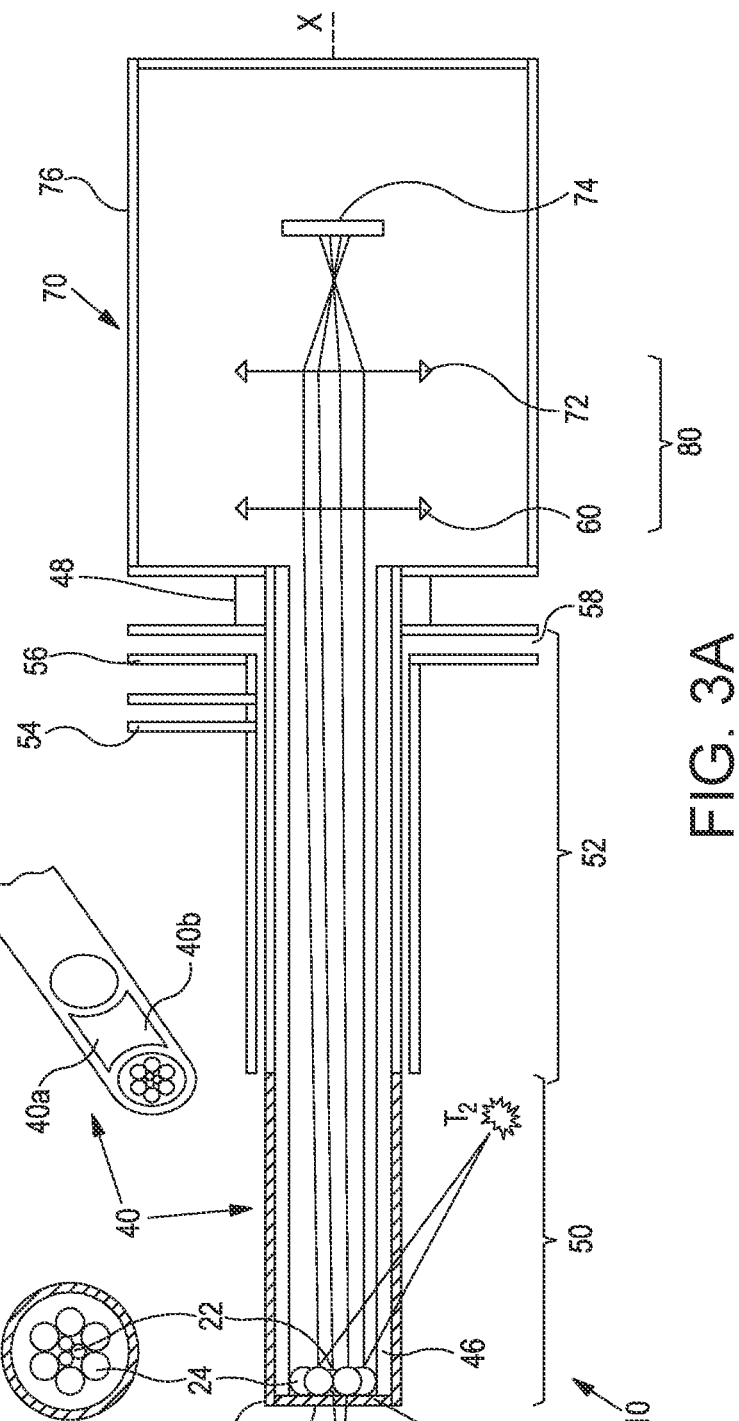
FIGS. 3A, 3B and 3C show an imaging device or system according to a second embodiment.

FIG. 3 shows an embodiment similar to FIG. 2, and like reference numerals and the relevant description above applies equally here and is not repeated.

In this embodiment, the first set of optics 20 comprises a plurality (three in the example shown, but it could be two or more) of refractive optical elements 22 such as lenses. These are surrounded by a plurality of reflective optical elements 24 as in FIG. 2, e.g. spherical reflective elements such as ball bearings 24—six in the embodiment shown. Other reflective elements could be used instead.

This arrangement provides a 3D forward view and 3D sideward/backward view. The 3D in side view is made possible by the multiple reflective elements 24 in the first optical system 20, which provides for disparity/distortion in images recorded at the sensor 74. The 3D in forward view is made possible by the multiple refractive elements 22 in the first optical 20 system which provides for disparity/distortion in images recorded at the sensor 74. See also the embodiment in FIG. 5H.

Figures 4A, 4B, 4C:
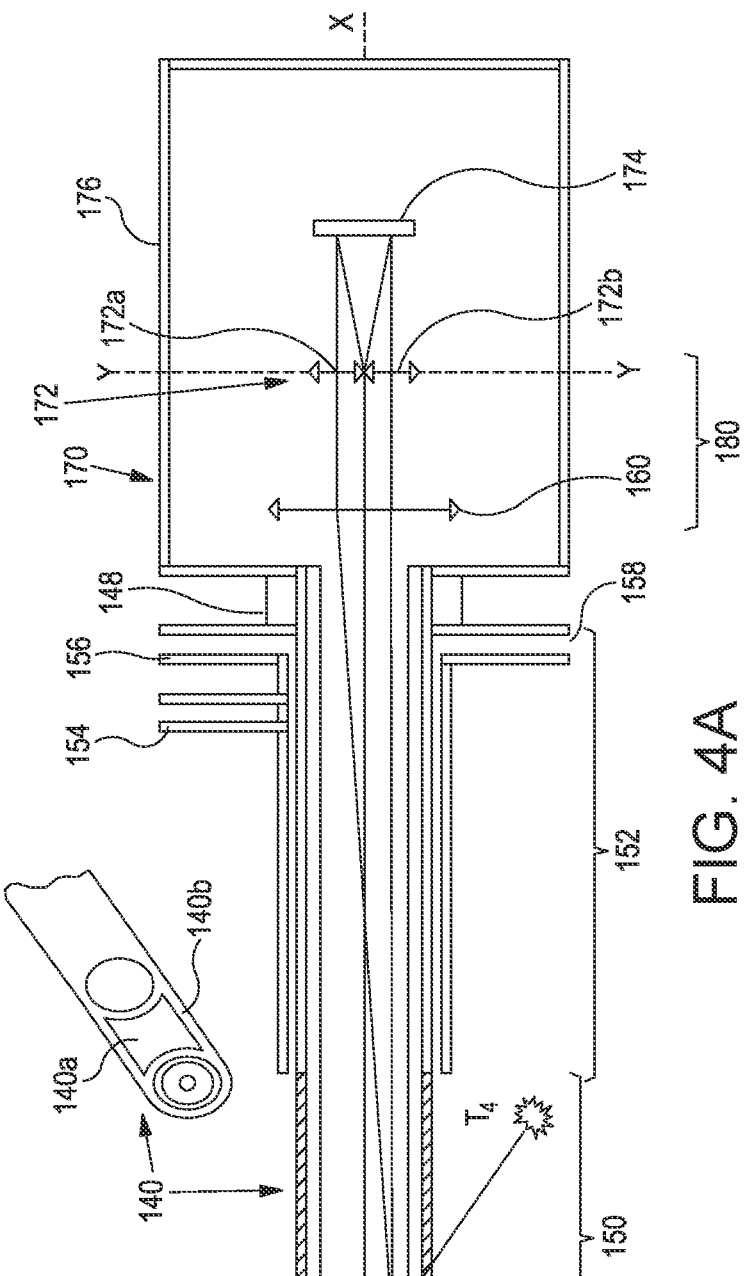
FIGS. 4A, 4B and 4C show an imaging device or system according to a third embodiment.

FIG. 4A shows an alternative embodiment of an imaging system 110. The imaging system 110 comprises a first optic 120. The first optic 120 comprises a central refractive optic 122 and a surrounding reflective optic 124. In the embodiment shown, the refractive optic 122 is a lens. The lens 122 is surrounded by a substantially spherical reflective element e.g. a substantially spherical reflective element such as a ball bearing. The lens 122 may be provided in a bore formed through a substantially spherical ball bearing 124 or in a reflective element comprising a central hole e.g. a torus shaped element. The lens 122 and bore are aligned along the axis X-X. This is shown in FIG. 4B. The optic 120 may be supported by a support structure (not shown in FIG. 4B; equivalent support structure 121 is shown in FIGS. 5A-5L). The support structure 121 may be transparent at least in part and/or opaque at least in part.

The optic 120 is housed within a longitudinal enclosure 140 and is aligned along the central longitudinal axis X-X of the enclosure 140. The plane of the first optic 120 is transverse to the longitudinal axis X-X. The first optic 120 is positioned at or near a first end 142 of the enclosure 140. The first end 142 of the enclosure has a window or opening 144 also aligned transverse to the longitudinal axis X-X. The window 144 may be or comprise plain glass or plastic or a focusing lens. As such, the planes of the first optic 120 and the window 144 are parallel to each other. The window 144 is transparent so as to allow light to enter the system 110. The window 144 may be or comprise glass or a plastics material. FIG. 4C shows an exemplary semi-open structure. Here, an inner glass tube 140a is surrounded by a steel "cage" or surround 140b that is transparent to the imaging device. In an embodiment, a transparent sheath may be covered or housed within a substantially open cage. The cage advantageously provides mechanical strength. The sheath may advantageously be waterproof and/or sealed.

The enclosure 140 is tubular, closed at the first end 142 save for the window 144 at the first end 142. The enclosure comprises a sleeve 146 of transparent material e.g. glass or plastic extending from the first end 142 to a second end 148. The sleeve 146 is sealed and may be formed of clear glass or plastic, to prevent contamination of the optical surfaces. A first portion 150 of the enclosure 140 starting at the first end 142 and extending towards a second end 148 of the enclosure 140 surrounds the sleeve 146 and is semi-open and e.g. formed of stainless steel. A second portion 152 of the enclosure starting from the innermost end of the first portion 150 and extending to the second end 148 is formed of a solid or non-transparent material e.g. solid stainless steel.

A light source (not shown) and light tube 154 are provided to direct light towards a subject to illuminate it for imaging. The light source may be an LED e.g. a white LED. A colour filter array (e.g. a Bayer filter mosaic) may be used to produce a colour image. The light source may be a repeating and/or alternating sequence of monochromatic wavelengths.

For example, red, green and blue light can be used. The resultant images can be combined to achieve a colour image. Additional wavelengths can be input to achieve other outputs. For example, where the system 110 is an endoscope, additional wavelengths can be input for advanced diagnosis techniques e.g. phosphorescent biological markers, oxy/deoxyhemolobin, short wave infrared for sub-surface imaging etc.

The enclosure 140 also has a fluid inlet 156 for directing e.g. pumping a fluid such as air, water and/or saline along the enclosure 140 to help keep it clean. The enclosure 140 may also have a fluid outlet 158 for removing used fluid from the system 110.

At the end 148 of the enclosure 140, there is a light capture system 170. The light capture system comprises a second optical system 180. The second optical system 180 comprises a second refractive optic 160 and third array of refractive optics 172. The light capture system 170 comprises the second refractive optic 160 and third array of refractive optics 172 and a light sensor such as a CMOS camera sensor 174. The third optic 172 comprises a plurality of refractive lenses. In the embodiment of FIG. 4A, four refractive lenses 172a and 172b are arranged in a plane Y-Z. (Two lenses 172a are adjacent each other and two lenses 172b are adjacent each other and adjacent the lenses 172a). The lenses 172a, 172b are aligned in a plane Y-Z along an axis Y-Y that is perpendicular to the longitudinal axis X-X of the enclosure. The fourth optic 172 and the sensor 174 are housed in a housing 176.

In use, a target $T_3$ can be imaged. Light from the light source is directed via light input 154 towards the target $T_3$. Light reflected from the target $T_3$ enters the enclosure 140 through window 144. The reflected light is transmitted through the first refractive optic 122 towards the sensor 174. The second lens 160 disperses the light to the third refractive optics 172a, 172b. Light refracted through the lenses 172a, 172b is captured by the sensor 174. An image 174' and/or image data from the sensor 174 can be transmitted to a computing/processing device for further processing in a conventional manner.

In this embodiment, the planar array optics 20 of FIGS. 2 or FIG. 3 are replaced with a single reflective optic 120, through which a refractive optic passes through the centre. Rather than the physical separation of the reflective surfaces to generate disparity exploited for 3D, the disparity is caused by the separation of two large refractive objects 172a, 172b contained in the image capture system 170.

The embodiment of FIG. 4 can provide for 3D imaging in the forward view and in sideward view. The 3D in the side view is made possible by the multiple refractive or reflective elements 172 in the second optical system 180 which provides for disparity/distortion in images recorded at the sensor 174. The 3D in the forward view is made possible by multiple refractive or reflective elements 172 in the second optical system 180 which provides for disparity/distortion in images recorded at the sensor 174. See also the embodiment in FIG. 5J).

This design is advantageously simpler to manufacture and allows 3D for all viewpoints—it could, as for FIG. 2 or 3—image the target $T_3$ in front of the window 144 and a non-aligned target $T_4$. As before, light reflected from the target $T_4$ can reach the first optic 120 because the first portion of the housing 150 is semi-open. The light is then further reflected by the ball bearing 124 towards the sensor 174. As for light reflected from $T_3$, the second optic 160 disperses the light to the third lenses 172a, 172b and to the sensor 174. The design of FIG. 4 also increases the useful collecting area of the sensor 174, which provides higher resolution raw images 174'. The separate views provided by lenses 172 of the light from the reflective elements/ball bearings 124 and the front lens 122 that provide multiple and overlapping viewpoints of the same regions in physical space enable a 3D image to be created.

Advantageously, for the embodiments of FIGS. 2, 3 and FIG. 4, the system 10, 110 can image targets in the full 360 in azimuth about the longitudinal axis X-X and between approximately +90° to −70° In elevation from the forwards direction backwards towards the axis X-X, i.e. a range of about 160° in elevation. As such, embodiments of the invention enable imaging in the "forward" (axial) and "sideward" (radial) directions and, to a more limited degree, the "backward" (axial) direction. This is achieved by having a plurality of reflective and/or a plurality of refractive optical components in the first and/or second optical system.

FIG. 5 illustrates various ways in which the invention can be implemented. In the following discussion, and with reference to the subfigures of FIG. 5, where there are a plurality of refractive and/or reflective optical components, this may be or comprise two, three, four, five, six or more refractive and/or reflective optical components arranged in a plane or not in a plane, adjacent and/or touching or not touching each other.

In FIG. 5A, a single ball bearing 24 forms the first optical system 20. This provides for both sidewards and backwards looking achieved through reflection off the reflective ball bearing 24 towards the sensor 74, 174.

In FIG. 5B, a single ball bearing 24, 124 forms the first optical system 20. This provides for both sidewards and backwards looking achieved through reflection off the reflective ball bearing 24, 124 towards the sensor 74. Unlike in (a), one or more additional lens elements 72, 172 in the image capture system 70, 170 allows a light-field image to be captured including angular information about the light rays from the subject reflected off the ball bearing. The lens elements 72, 172 are provided in the radial plane, offset with respect to the X-X axis. The multiple refractive or reflective elements 72, 172 in the second optical system 80, 180 provides for disparity/distortion in images recorded at the sensor 74, 174. The angular information allows "triangulation" of the source (subject) and hence a 3D image to be reconstructed.

In FIG. 5C, alternatively to 5B, rather than additional lenses in the camera, the same effect can be achieved through multiple reflective elements 24 in the first optical system. Here the sidewards field of view is restricted due to obscuration of the neighbouring reflective element 24.

In FIG. 5D, the loss due to obscuration observed for FIG. 5C can be recovered through introduction of a second plane of reflective elements (perpendicular to the longitudinal axis). The reflective elements 24, 124 in first imaging system 70, 170 are in more than one planar array which provides for disparity/distortion in images recorded at the sensor 74, 174. In an alternative embodiment, the reflective elements 24, 124 could be in a non-planar array.

In FIG. 5E a refractive (e.g. lens) element 22, 122 amongst the reflective elements 24, 124 allows for a 2D forward looking view. In this embodiment, the refractive element 22, 122 provides a forward view as well as a 3D sideways view. Advantageously, however, the construction and/or arrangement is simple.

In FIG. 5F, like in FIG. 5D, the sidewards and backwards looking 3D view can be increased through employing a second (or multiple) plane(s) of reflective elements 24, 124.

In an alternative embodiment, the reflective elements 24, 124 could be in a non-planar array.

In FIG. 5G, similar to FIG. 5F, additional lens elements 72, 172 in the image capture system 70, 170 allow a light-field to be captured enabling 3D for all views. By providing multiple lenses 172 in the second optical system 80, 180, this provides for generating a disparity and for 3D imaging in the forward view.

In FIG. 5H, alternatively, but with a limited sidewards and backwards looking view, multiple refractive lens elements 22, 122 could be used at the reflective plane 20 (with reflective elements 24, 124) to allow forward looking 3D as well as 3D in the side view. Similar to FIG. 5E, by introducing a plurality of reflective elements 24, 124 in/at the first imaging system, this provides for generating a disparity and for the forward/side 3D imaging.

In FIG. 5I, the forward looking lens 22, 122 may be embedded within the reflective element 24, 124.

In FIG. 5J, similarly to 5B, multiple lenses 72, 172 in the image capture system 70, 170 allow for a light-field image giving 3D information in all directions. By providing multiple lenses 72, 172 in the second optical system, it is possible to generate a disparity and image in 3D in the forward and sideways views.

In FIG. 5K, Rather than discrete reflective 24, 124 and refractive 22, 122 elements, the profile of a homogenous transparent material 223 allows for a combination of refraction and total internal reflection to generate forward and limited sidewards looking viewpoints.

In FIG. 5L, again similar to 5B, additional lens elements 72, 172 in the camera 70, 170 allow a light-field to be generated allowing for 3D information in each view. By introducing multiple lenses 72, 172 in the second optical system it is possible to generate a disparity and image in 3D in the forward and sideways views.

The arrangement of optical elements in the embodiments of FIGS. 5K and 5L provide for total internal reflection of light passing through the device 10, 110. The arrangement of optical elements in the embodiments of FIGS. 5K and 5L provide for total internal reflection of light passing through the device 10, 110. The arrangements of FIGS. 5K and 5L may be achieved by providing the first optical system with an optical element 223 that takes the place of separate refractive and reflective elements. The optical element may be formed e.g. machined into the distal end of the device (which may be a cylinder of glass or plastic). It includes one or more surfaces 22', 122' that are profiled to create a forward looking refractive lens and one or more surfaces 24', 124' that utilise total internal reflection to give a side view. At the proximal end of the device one surface (e.g. as in FIG. 5K which provides for non-3D imaging) or more than one surface (e.g. as in FIG. 5L which does provide for 3D imaging) 72, 172 can be provided that act as refractive lens(es) to direct the light onto the sensor. The optical element 60, 160 is optional.

The system 10, 110 as described above can be used to obtain images of a target T. The enclosure 40, 140 is represented in the figures as a body cavity, of cylindrical cross-section, and closed at the far (upper) end. Depending on the particular optical arrangement, the image capture system 70, 170 captures 2D and/or 3D images as illustrated schematically in FIGS. 5A-L. More specifically, the sensor 70, 170 captures 2D images that can be processed to extract 3D information.

Figures 6A, 6B:
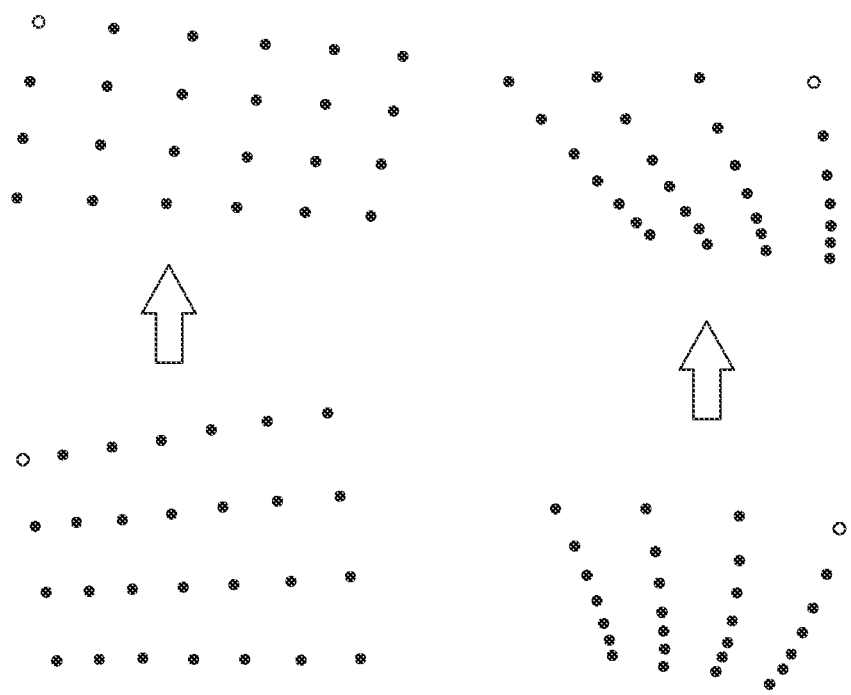
FIGS. 6A and 6B depicts the concept of disparity and distortion.

FIGS. 6A and 6B illustrate a disparity that may be observed using the arrangement of any of FIGS. 2 to 5. In 6A, disparity between a grid of dots as viewed from two viewpoints (e.g. conventional stereo) is illustrated. A distortion between images/views of a feature as imaged using two different optical components would provide a similar effect. In FIG. 6B, the grid of dots is additionally reflected off a curved surface e.g. an optical element such as a ball bearing, which additionally shows a distortion of the image.

Figure 7A:
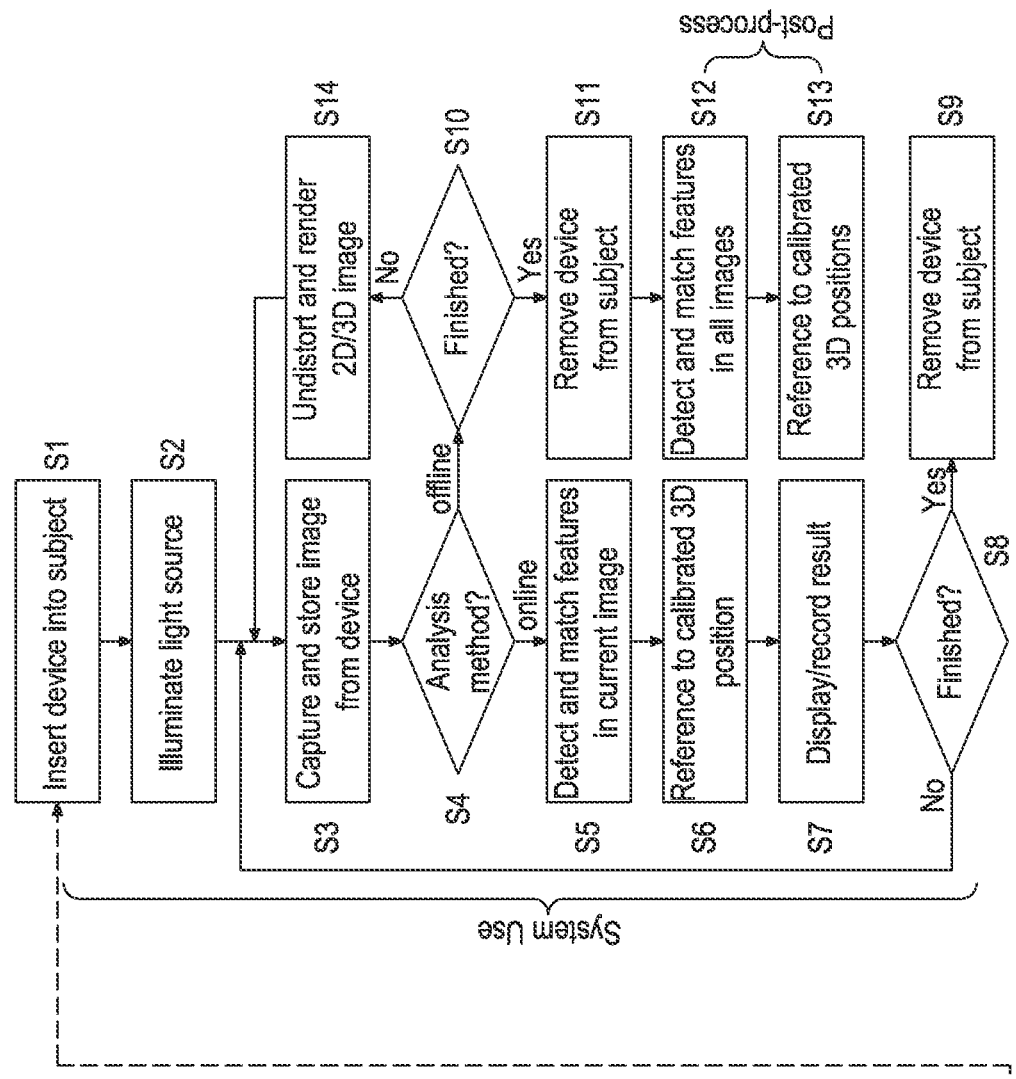
FIGS. 7A and 7B show a calibration process.

FIG. 7 illustrates an exemplary process flow for obtaining an image using the system of FIGS. 2A to 5.

At step S1, the device 10, 110 is inserted into a patient, subject or area to be investigated. A light source is illuminated at step S2. The image capture system 70, 170 is controlled to capture an image in step S3, e.g. by a control unit or processor operating in a conventional manner. In step S4, the captured image may be stored e.g. In a local or remote memory device, again in a conventional manner.

The captured/stored image may then be analysed "online" or "offline"—step S4. "Online" processing happens in real-time and may be performed on the incoming image or on the stored image; "offline" processing occurs not in real time and on the stored image.

Steps 5 to 8 relate to the online mode. Here, in step S5, features of the subject/area being imaged are detected in the raw/stored images obtained from different lens groups. For example, there are four lenses 172 in FIG. 4—two upper lenses 172a and two lower lenses 172b (as the device is shown in FIG. 4). Corresponding features are looked for in the different images (from the different lenses 172a, 172b) i.e. corresponding features that relate to the same target/object can be matched in step S6. The results may be displayed or recorded in step S7. At step 8 if the process has finished, the device is removed from the subject in step S9, otherwise the process returns to step S3.

Steps 10 to 13 relate to the offline mode. Here, in step S10 a determination is made that the process is finished (i.e. the data will be analysed later). In step S11, the device is removed from the subject. Offline/post-processing occurs in steps S12 and S13 where features of the subject/area being imaged are detected in the stored image. These features are then matched across all images taken in step S12. The results are also compared to calibrated 3D positions to determine the actual location of the feature that was imaged (step S13). The output may be displayed or recorded.

Alternatively, at step S10, if the process has finished, the image is undistorted and rendered (steps S13) and the process returns to step S3.

As such, the plurality of reflective and/or refractive optical components of aspects and embodiments of the invention provide for obtaining a plurality of images that can be processed to extract 3D information. The different images obtained from each reflective and/or refractive optical component will provide an image where a feature or object of interest is in a different location in 2D or 3D space ("disparity") and/or which has a different shape or size due to "distortion" from imaging from the optical component(s).

Figure 8:
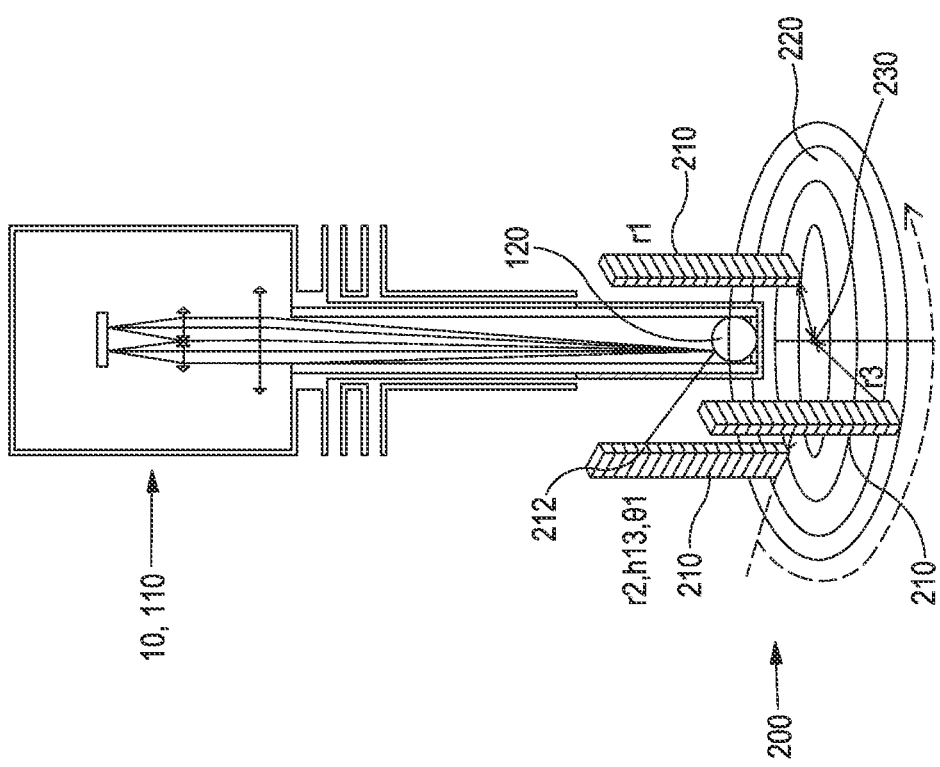
FIG. 8 depicts a calibration method used with the device or system of FIG. 1, 2A, 2B, 2C, 2A, 2B, 2C, 4A, 4B, 4C or 5A to 5F.

The images can be calibrated as discussed below. FIG. 8 shows a calibration system 200 that can be used with the imaging system 10, 110 (system 110 is shown in FIG. 8 by way of example). The calibration system 200 comprises a plurality of light arrays e.g. bargraph LED arrays 210. Three are shown in FIG. 8, but it will be appreciated that more or fewer may be used. The LED arrays 210 are mounted on a rotatable stage, e.g. a precision rotation stage 220. The longitudinal LED arrays 210 are mounted transverse to the stage 220 with the longitudinal axis of each array 210 extending in the same direction. The stage 220 has a centre point 230 (preferably it is a substantially circular stage). Each array 210 is located at different distances or radii from the centre point 230. In the embodiment shown, the three arrays 210 are located at radii $r_1$, $r_2$ and $r_3$, where $r_1 \neq r_2 \neq r_3$. The imaging system 10, 110 is positioned with its longitudinal axis aligned with those of the arrays 210, and along the axis running through the centre point 230 and perpendicular to the plane of the stage 220. The arrays 210 are positioned so that their widths are radially aligned with the centre point 220.

Alternatively, a single display screen e.g. an OLED display screen (not shown) may be used, positioned at a single radius from the centre 230 of the stage 220. The array 220 may be offset by a small angle (rather than being radially aligned as above) such that the viewing angles of the OLED pixels are sufficient to cast light on the system 10, 110.

In either embodiment, the arrays 210 can freely move around the imaging system 10, 110.

The length (or height) of the arrays 210 is approximately the same as, or less than, the length of the first, semi-open window portion 50 to allow illumination from the arrays 210 to be imaged by the system 10, 110.

Figure 7B:
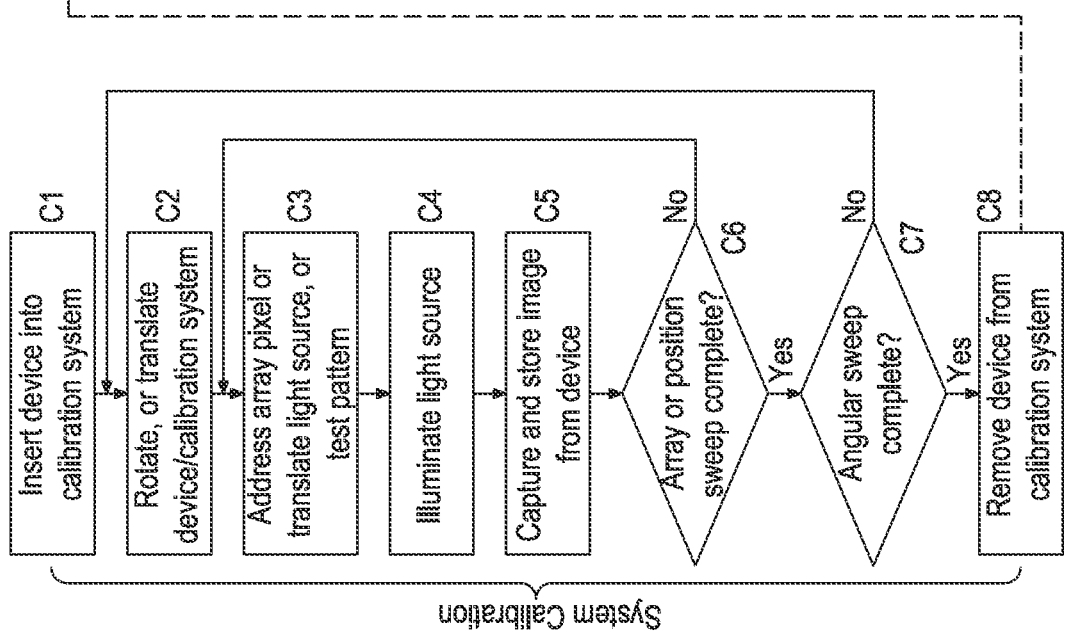

With reference to the above and also to FIG. 7B, in use, the device 10, 110 is inserted into the calibration system 200 (step C1). In step C2 (optional, at least for initial use, the device 10, 110 and/or the calibration system 200 is rotated (step C2). In step C3 the calibration control process is initiated. The device 10, 110 is known to be a particular location/position and a control signal is sent to an array pixel or to translate the light source or initiate a test pattern. In an embodiment, a single LED 212 of the array 210, or OLED pixel (or cluster), is illuminated (step C4).

The LED 212 is at a predefined distance or radius r from the centre of the stage 220, is at a particular height h above the plane of the stage 220 and is at a particular angle with respect to a reference radius (not shown) in the rotational plane of the stage 220. In the embodiment of FIG. 8, the identified pixel 212 is at a radial distance r2 from the centre 230 of the stage 220, at a height h13 above the stage 220, and at an angle $\theta 1$ with respect to the rotational reference radius.

At least the vertical pitch of the LEDs 212, the horizontal and vertical pitch of the OLED/OLED clusters, the steps in radii and the steps in rotation together define the measurement precision of the system 10, 110, and can be tuned.

The illumination from that LED 212 is incident on the reflective optic 120. The LED 212 acts as a target T and, in accordance with the procedure described above, the light enters the device 10, 110 and an image 74', 174' of the LED light is produced and recorded by the camera 174 (step C5; see FIG. 9). In the embodiment shown, which is for the device 110 of FIG. 4, there are four separate lenses 72, and so four separate images 74a', 74b', 74c', 74d' (or 174a', 174b', 174c', 174d') are obtained. (NB. Images of the refractive elements can be seen in the central part of each of the images 74a', 74b', 74c', 74d' (or 174a', 174b', 174c', 174d'). A representation 212' of the pixel 212 is seen in each image 74', 174' observed at/taken by the sensor 74, 174. This references the pixel 212 and its known location in physical space to the pixel image 212'. The stage 220 is then rotated in angular increments through the full 360° of rotation, and/or translated in increments, and or additional LEDs are illuminated and the process repeated. Any suitable angular increment could be used that is sufficient to advance the device 10, 110 relative to the calibration system 200. A check is performed to see if the array position sweep is complete, i.e. if all elements of the array have been imaged—step C6. If not, the process returns to step C3. The process may also be repeated and an average taken for greater accuracy (step C6 to C9). One or more of the remaining LEDs 212 are then illuminated, and/or the stage 220 is rotated in angular increments (preferably the same angular increments) or translated, and imaged in the same way, until the complete measurement volume has been occupied by an illuminated LED (step C7). The calibration results are stored in a lookup table e.g. in a storage device on a computer, tablet, other processor either on the device 10, 110 or remotely. The lookup table can be used to identify, for an LED/pixel 212' image detected at the camera 74, 174, an originating point in space for the illumination. One or more known LED 212 locations are therefore calibrated to positions as imaged by a particular device 10, 110. When complete, the device 10, 110 is removed from the calibration system 200.

FIG. 10A shows an example image (the 'raw', unprocessed image) 74, 174' captured by the sensor 74, 174. A processing or control system (not shown) is provided for processing the image data collected. The individual views 74a', 74b', 74c', 74d' (or 174a', 174b', 174c', 174d') may be isolated and saved and processed separately. Feature F is seen as $F_a$ in FIG. 10A, as $F_b$ in FIG. 10A, as $F_c$ in FIG. 10A and $F_d$ in FIG. 10A. FIG. 10B shows just the image of image 74a', 174a'. The image 74a', 174a' is interrogated for features F different to the expected image if there was no illumination. The other three images 74b', 74c', 74d' (or 174b', 174c', 174d') are then searched to try to identify the same feature F. The same feature F will look different in each image ($F_a$, $F_b$, $F_c$, $F_d$) because of the different spatial position of the lens 172 from which the image originated. The identified, common features 300 are identified/calculated and may be displayed on a processed image 74a", 174a", as exemplified in FIG. 10C. The lookup table is used to calibrate where the feature was in real space when the images were simultaneously taken.

FIGS. 11A-F show examples of unique features 300 that have been found in a first image 74a', 174a' of a target, and matched in the alternative view images 74b', 74c', 74d' (or 174b', 174c', 174d'). Only those common identified features 300 that lie within the epipolar constraint (i.e. restriction due to the size of the arrays) are considered as valid features 300. Such validated features 300 are then referenced in the lookup table to determine the position in 3D space from which the illumination originated i.e. where the target is.

Figure 11C:
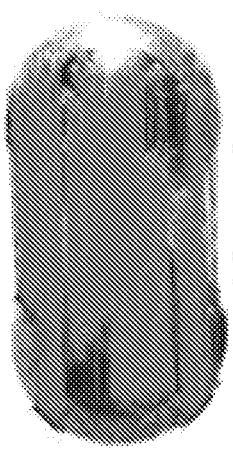
FIGS. 11A to 11F show exemplary images taken and used during post-processing of image data.
Figure 11F:
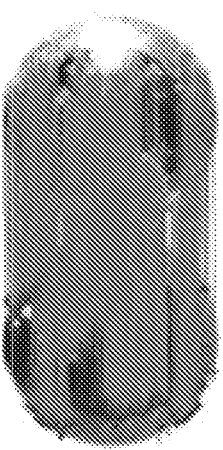
Figure 11B:
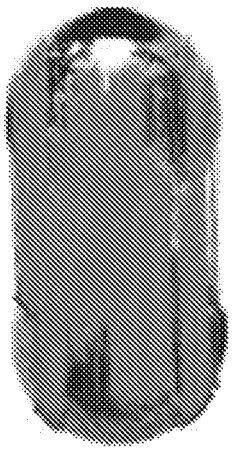
Figure 11E:
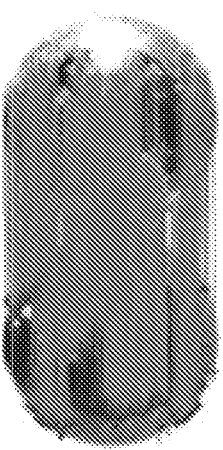
Figure 11A:
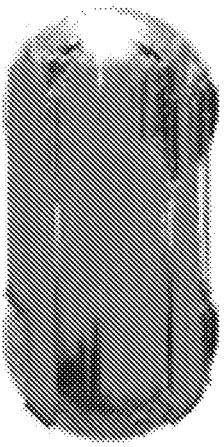
Figure 11D:
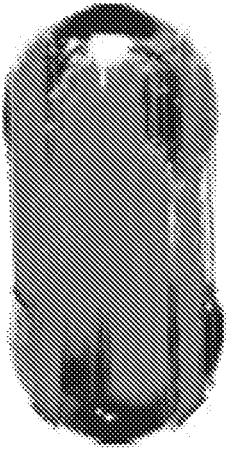

FIG. 11A exemplifies features matched between image 74a' and 74b'. FIG. 11B exemplifies features matched between image 74a' and 74c'. FIG. 11C exemplifies features matched between image 74a' and 74d'. FIG. 11D exemplifies features matched between image 74b' and 74c'. FIG. 11E exemplifies features matched between image 74b' and 74d'. FIG. 11F exemplifies features matched between image 74c' and 74d'. I.e. all possible image comparisons are performed.

The system 10, 110 may have one or more other features, some of which are described below.

As discussed above, targets or other features are imaged by picture elements (pixels) within the CMOS camera sensor 74, 174. The image quality is defined by the number of pixels that sample the feature, and can be expressed as the 'native' resolution of the sensor in terms of pixels per mm. To increase the effective resolution of images and features, the established technique of super-resolution can be used. A temporal sequence of 'native' resolution images with sub-pixel misalignments can be co-added into a higher resolution array, so long as the sub-pixel misalignments can be measured, to produce higher resolution or 'super-resolution' images. With camera frame rates in excess of 30 FPS (and ideally 60 FPS) and the natural movement of the operator, sufficient 'native' resolution images can be acquired to produce super-resolved images for a user to view without noticing the processing that is involved.

A conventional 2D image can be generated in real-time for a user, by applying a spherical undistortion algorithm to any of the viewpoints, either from raw or super-resolved images. The viewing angle can be chosen in real-time by GUI manipulation.

A conventional 2D image can be generated in real-time for a user by applying a fisheye lens undistortion algorithm, either from raw or super-resolved images.

The path of the system 10, 110 through the subject is generated using a Visual Odometry technique. The changing relationships and positions of features are used to estimate the camera pose and rotation between a sequence of images in time. These are then used to generate the trajectory taken.

Distortions to the images arising from movement of the subject and bubbles and turbulence of any potential intermediate fluids are identified and rejected from analysis in a similar method to the 'Lucky Imaging' technique. Lucky imaging is commonly used in ground-based amateur astronomy to remove atmospheric distortions from celestial images before stacking to improve Signal to Noise Ratios.

Aspects and embodiments of the invention may be applied to a variety of different electronic imaging uses. One particularly useful application is in medical imaging. The system 10, 110 may be an endoscope.

From reading the present disclosure, other variations and modifications will be apparent to the skilled person. Such variations and modifications may involve equivalent and other features which are already known in the art, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

It is to be specifically noted that arrangements of single or plural reflective and/or refractive elements in the first and/or second optical systems other than those shown in the accompanying drawings can be used to generate 3D information. These are specifically encompassed within the scope of aspects and embodiments of the invention.

Features which are described in the context of separate embodiments may also be provided in combination in a single embodiment. Conversely, various features which are, for brevity, described in the context of a single embodiment, may also be provided separately or in any suitable sub-combination. The applicant hereby gives notice that new claims may be formulated to such features and/or combinations of such features during the prosecution of the present application or of any further application derived therefrom.

For the sake of completeness it is also stated that the term "comprising" does not exclude other elements or steps, the term "a" or "an" does not exclude a plurality, a single processor or other unit may fulfil the functions of several means recited in the claims and any reference signs in the claims shall not be construed as limiting the scope of the claims.

The invention claimed is:

1. A method of calibrating an imaging device having a longitudinal axis, the method comprising the steps of:
   positioning a said imaging device with respect to one or more light sources or test patterns each having a longitudinal axes so that their longitudinal axes are aligned with that of the imaging device;
   changing the relative position of the imaging device relative to the one or more light sources or test patterns;
   selectively activating or selecting the one or more light sources or test patterns at a plurality of different angular positions; and
   using a sensor or camera in the imaging device, sensing light emitted from or imaging the light source or the test pattern.

2. The method of claim 1 comprising positioning an imaging device with respect to the sensor arrays of the calibration system.

3. The method of claim 2, comprising turning on a single light element and recording an image of that light source or test pattern.

4. The method of claim 3, comprising rotating the imaging device or light arrays by a predefined increment and taking another reading.

5. The method of claim 1, wherein the light source or sources or test patterns may be or comprise an array of individually controllable or selectable light sources or test patterns.

6. The method of claim 1, wherein the arrays are mountable to a rotatable stage or support, or the imaging device is mountable to a rotatable stage or support, or wherein the light sources or test patterns are freestanding or fixed to multiple translation stages.

7. The method of claim 1, wherein a plurality of light source or test pattern arrays are utilised, positioned at different distances from the centre of the stage.

8. The method of claim 2, further comprising aligning the sensor arrays of the calibration system with the centre of the stage.

9. The method of claim 4, further comprising referencing the image to known measurements in 3D space.

* * * * *